United States Patent [19]

Kuramochi et al.

[11] Patent Number: 5,305,641
[45] Date of Patent: Apr. 26, 1994

[54] METHOD FOR EVALUATION OF ACOUSTIC ANISOTROPY AND MEASURING APPARATUS THEREFOR

[75] Inventors: Mitsugu Kuramochi; Yoshitaka Yabe, both of Tokyo, Japan

[73] Assignee: Shimizu Construction Co., Ltd., Tokyo, Japan

[21] Appl. No.: 760,336

[22] Filed: Sep. 16, 1991

[30] Foreign Application Priority Data

Sep. 17, 1990 [JP] Japan ................................ 2-246536

[51] Int. Cl.[5] .......................................... G01N 29/18
[52] U.S. Cl. ...................................... 73/598; 73/627; 73/645
[58] Field of Search ................. 73/597, 594, 598, 599, 73/644, 645, 632, 633, 627

[56] References Cited

U.S. PATENT DOCUMENTS

| | | | |
|---|---|---|---|
| 4,033,182 | 7/1977 | Clotfelter | 73/627 |
| 4,138,894 | 2/1979 | Robert et al. | 73/645 |
| 5,176,033 | 1/1993 | Jones et al. | 73/644 |

OTHER PUBLICATIONS

Japanese Industrial Standard JIS Z 3060-1988, entitled Methods of Manual Ultrasonic Examination and Classification of Test Results for Ferritic Steel Welds, Sec. 5.10 p. 19 to Sec. 5.10.6 "Certification of Acoustic Anistropy" on p. 21.

Document published by the Architectural Institute of Japan (AIJ) 1989, as a supplement of JIS Z 3060-1988. "Standard For The Ultrasonic Inspection Of Weld Defects In Steel Structures", pp. 109–113, 114–124, Lines 18–21.

"Ultrasonic Measurement of Sheet Anisotropy and Formability" by A. V. Clark et al., SAE Technical Paper Series, Feb. 27–Mar. 3, 1989 (pp. 89–95).

"Ultrasonic Measurement of Formability in Thin Ferritic Steel Sheet" by A. V. Clark et al., 1988 Review of Progress NPE, La Jolla, Calif. Aug. 1988 (pp. 1–8).

"Stress-Induced Anistrophy in Solids—The Acousto–Elastic Effect" by R. J. Smith, Ultrasonics/Jul.-Sep. /1963 pp. 135–147.

*Primary Examiner*—Hezron E. Williams
*Assistant Examiner*—Rose M. Finley
*Attorney, Agent, or Firm*—Biebel & French

[57] ABSTRACT

Increasing use of thermo-mechanically treated high strength steels in construction projects has created a need for on-site inspection of welded joints by ultrasonic techniques. However, such steels are acoustically anisotropic, and corrections of test results for anisotropy, according to the traditional methodologies, require lengthy and complex preparation steps which are unsuitable for on-site testing. The present invention presents an automated quick and simple methodology, and a compact apparatus for determining the acoustic anisotropy in such materials. The apparatus is expected to lead to effective management of quality assurance not only in civil and architectural engineering projects but in heavy machinery and ship building industries.

7 Claims, 9 Drawing Sheets

$\theta = \tan^{-1}(Y/2t)$

FIG. 9(c)
65 DEGREES

FIG. 9(d)
70 DEGREES

METHOD FOR EVALUATION OF ACOUSTIC ANISOTROPY AND MEASURING APPARATUS THEREFOR

BACKGROUND OF THE INVENTION

1. Field of the Invention

The present invention relates to an improved method of evaluating acoustic anisotropy of construction materials, and an apparatus for performing such a task. It is especially useful for ultrasonic inspection of welded joints in architectural or civil engineering structures in which acoustic anisotropy of the test material presents difficulties in interpretation of the inspection results.

2. Background Art

Modern technological advances have placed increasing demands on the performance of superstructure buildings which contain sophisticated data communications equipment. Such buildings need to retain structural integrity under much more severe loading conditions, including seismic conditions, than conventional structures. Increasing numbers of modern buildings utilize super high strength construction steels, and the builders resort to ultrasonic technique to inspect the integrity of welded joints. Therefore, the efficiency of ultrasonic inspection procedure directly affects the productivity of such construction projects.

Typical of materials for buildings are high strength steels made by thermo-mechanical control processes (known as TMCP steels). These steels are produced by rolling at temperatures lower than those used for normal hot rolling steels, thus producing steels having a high acoustic anisotropy. In such steels, the velocity of propagation of the ultrasonic beam is different in the longitudinal and transverse directions. It is difficult to apply ultrasonic inspection techniques to such steels, because the propagation speed differences in the two directions contribute to misinterpretation of ultrasonic inspection results caused by false refractions. Therefore, there has been a long outstanding need for a weld inspection methodology and apparatus which would enable quick and accurate checking of welds in such TMCP steels.

Weld inspection procedures for acoustically anisotropic steels are standardized in the Japanese Industrial standard (JIS) No. Z 3060, hereinafter referred to as JIS, entitled "Methods of Manual Ultraionic Examination and Classification of Test Results for Ferritic Steel Welds". Ultrasonic inspection techniques are also defined in another standards, "Standards for the Ultrasonic Inspection of Weld Defects in Steel Structures", published by the Architectural Institute of Japan, hereinafter shortened to AIJ.

In the JIS, a transverse beam normal probe, which produces through-thickness travelling beams (hereinafter referred to as vertically-acting), to measure the velocity ($C_{sl}$) in the primary rolling direction (i.e. in the longitudinal direction), and the probe then measures a transverse beam velocity ($C_{sc}$), from which a sound velocity ratio ($C_{sl}/C_{sc}$) is calculated to determine whether there is acoustic anisotropy. A material is considered to have acoustic anisotropy when this ratio exceeds 1.02. Next, the angles of refraction data of the material, obtained with the use of a pair of angle-probes according to a so-called "V through scan method", are corrected by using the measured value of acoustic anisotropy and the standard test block (STB). There are regulations concerning the calibration of the measuring apparatus with a comparative testing block (RB-4), as well as the use of probes having a 60 degree refraction angle.

The AIJ regulation also mandates the use of the STB and the sound velocity ratio to correct the measured angles of refraction of the specimen.

These methods for the TMCP steels are much more complicated and time consuming than for the regular steels, because they are based on a two step process of: first determining the degree of acoustic anisotropy followed by the corrections of measured angles of refraction. Such requirements for the testing protocol adversely affected the efficiency of inspection, and ultimately added to the overall cost of construction projects which utilized TMCP steels.

Further practical problems with the existing method of determining the acoustic anisotropy are explained below.

In the measurements of the sound velocity ratio $C_{sl}/C_{sc}$ from which acoustic anisotropy is obtained, it is necessary to measure the values of $C_{sl}$ and $C_{sc}$ very accurately. This operation required excessive time, and contributed greatly to lengthening of the testing period, and the consequent loss in construction productivity.

Further, the JIS requires the use of a comparative testing block (RB-4) to calibrate the testing apparatus, and this requirement was extremely difficult to be met in an environment of on-site construction activities. This further added to the cost of testing.

Further, the testing standards specify the use of either a 60 or 65 degree probe, irrespective of the degree of acoustic anisotropy of the construction material. Although construction materials come in a large variety of different shapes (for example, H-beams, rectangular beams and pipes) and their angles of bend and thicknesses have to be taken into account individually in order to obtain best results, there is no allowance for using probes having other angles.

The most serious drawback of the present method is that, in spite of the wide recognition of the importance of such testing, the method of acoustic anisotropy determination is being utilized only in large construction projects because the current methodology does not appeal to general construction industries.

SUMMARY OF THE INVENTION

The present invention presents solutions for the above mentioned problems caused by the current methodology of determining the acoustic anisotropy of high-strength building materials. The invented methodology is applicable not only to architectural and civil engineering projects, but to other general construction activities involving fabrication of ships and heavy machineries.

Specifically, the present invention relates to a method and an apparatus for determining the acoustic anisotropy of materials readily and speedily.

The invented method of determining the degree of acoustic anisotropy in a construction material 21 with a single transducer comprises the step of:

(a) injecting two mutually perpendicular beams of ultrasonic pulses vertically into a material 21, wherein the direction of propagation of one of said beam of pulses coincides with the main rolling direction of the material 21;

(b) detecting simultaneously the reflected pulses in the longitudinal and transverse directions, and calculating the velocities of travelling pulses, $C_{sl}$ and $C_{sc}$, in the longitudinal and transverse directions, respectively, and calculating a ratio of ($C_{sl}/C_{sc}$) for the material;

(c) computing the velocity ratio ($C/V_{stb}$) in a standard test block (STB), from a predetermined experimental relationship of the velocity ratios between the material and the STB, wherein C is a constant for the STB and $V_{stb}$ is the velocity of pulses in the STB;

(d) determining the deviation in the angle of refraction ($\theta - \theta_{stb}$), based on a predetermined experimental relationship of said velocity ratio ($C/V_{stb}$) and the refraction angles in the STB, wherein $\theta$ is the refraction angle in the material and $\theta_{stb}$ is the refraction angle in the STB; and (e) determining the degree of acoustic anisotropy in the material 21 from the measured deviation, in step (d), in the value of refraction angles from the standards.

The method can also be applied for determining the acoustic anisotropy with two transducers: a transmitter probe and a receiver probe in a construction material 11 through the steps of:

(a) injecting ultrasonic defect searching beam of pulses (searching beam hereinbelow) into a material 11, at an inclined angle to the main rolling direction of the material 11;

(b) measuring simultaneously the velocities of the reflected pulses in the longitudinal and transverse directions, $C_{sl}$ and $C_{sc}$, respectively;

(c) obtaining the refraction angles ($\theta 1$, $\theta c$) of mutually perpendicular searching beams and the difference ($\triangle \theta$) in their refraction angles, based on the measurements from (b); and (d) determining the degree or absence of acoustic anisotropy in the material 11.

The methodology is applicable to: the vertically-acting shear wave probe method (VAM); to the angle probe method with one probe (SAM1); and to the angle probe method with two probes (SAM2). The method provides a rapid and simplified process of determining the acoustic anisotropy in construction materials compared with the conventional methods.

The present invention also presents an apparatus A for carrying out the above described steps to determine the degree of acoustic anisotropy in a material 21.

The apparatus A comprises:

(a) a generating means for generating two mutually perpendicular ultrasonic pulses;

(b) a vertically acting shear wave probe 22 for injecting a beam of pulses into the material 21 vertically and detecting the reflected beam, in the longitudinal and transverse directions, simultaneously;

(c) an injecting means for injecting a beam of pulses at an angle to the main rolling direction of a material 11;

(d) a detection means 1 comprising an angle probe 12 for detecting simultaneously the reflected beams, in the longitudinal and transverse directions;

(e) a decision means 11 to determine the degree of acoustic anisotropy in said material 21 based on the information derived from STB velocity ratio, the magnitude of deviations in the STB refraction angles;

(f) decision means 12 and 13 to determine the degree of acoustic anisotropy in said material 11 based on the information derived from refraction angles and the deviations in the refraction angles;

(g) a display means 7 for displaying computed results;

(h) selecting means, according to input from instruction means 3, for selecting a method for acoustic anisotropy determination from a group consisting of vertically-acting shear wave probe method, the angle probe method with one probe and the angle probe method with two probes.

With the above described apparatus of the present invention, it is possible to determine the degree of acoustic anisotropy in materials 21 and 11 rapidly and simply, thus contributing greatly to the efficiency of on-site construction projects. Compared with the conventional apparatus, the invented apparatus is compact and simple to operate, thus contributing greatly to reducing the inspection cost and duration of construction projects.

The method of single angle probe does not require special searching beam facility or couplant, and is applicable within the framework of the methodology of the traditional single angle probe method.

The apparatus also permits the use of an angle probe having a 45° or a 70° angle which were not adaptable to the conventional ultrasonic fault detection equipment.

BRIEF DESCRIPTION OF THE DRAWINGS

FIG. 5 (a) and (b) show partial steps for decision means.

FIG. 4 (a) to (d) are graphs showing the relationship between the velocity ratios in STB ($C/V_{stb}$) and the deviation in refraction angles in STB ($\theta - \theta_{stb}$).

DETAILED DESCRIPTION OF THE PREFERRED EMBODIMENTS

The present invention is explained below in reference to the preferred embedments described below together with the figures to explain the important features of the invention.

Figure 1:
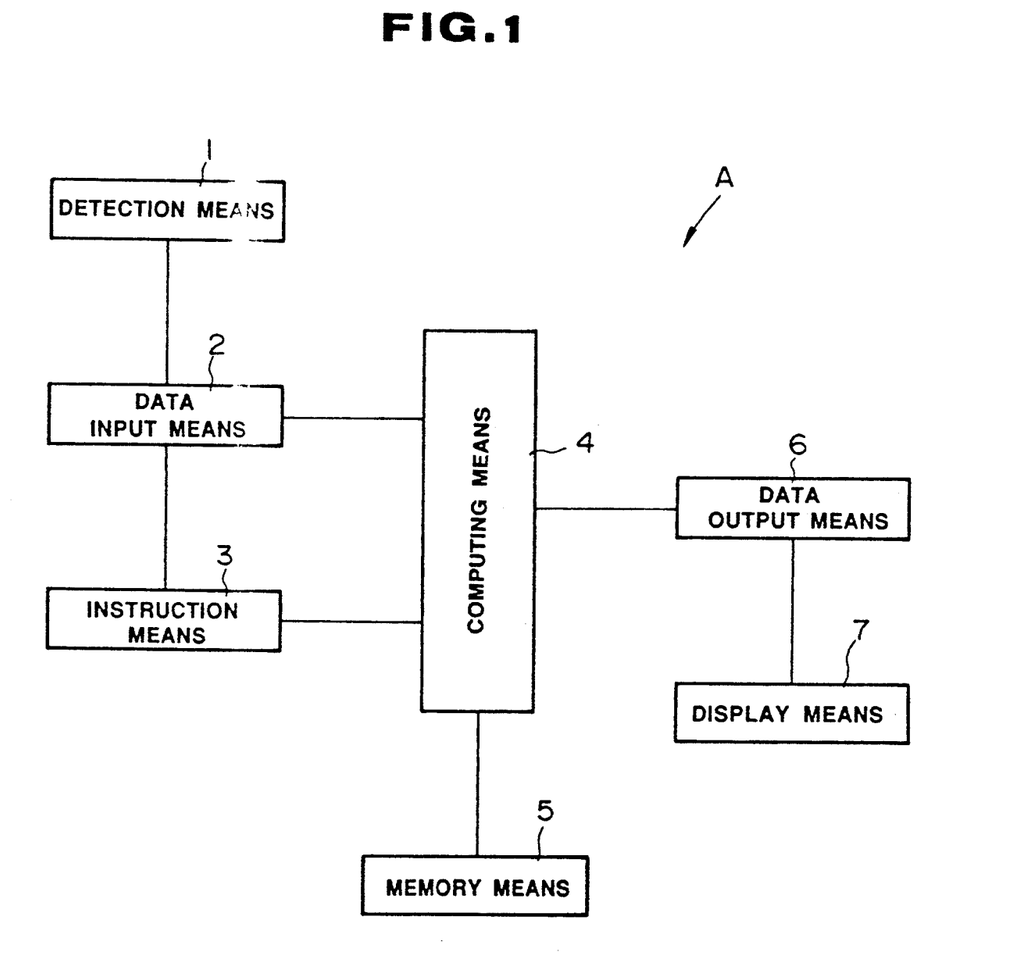
FIG. 1 is a block diagram for an acoustic anisotropy determination apparatus.

First, the overall concept of ultrasonic testing is explained in FIG. 1 which is a block diagram of the main components of the apparatus A for determining the acoustic anisotropy of materials. The basic components include: detection means 1; data input means 2; instruction means 3; computing means 4; memory means 5; data output means 6; and display means 7.

The detection means 1 is constructed so that a double-structured vibrating element produces ultrasonic pulses in two mutually perpendicular directions, and a beam producing device which can inject beam of pulses in the direction to coincide with the primary rolling direction of the test material. The detection means 1 consists of two components: the first detection means produces a vertically-acting beam of shear waves (VAM) and a second detection means comprising an angle probe which transmits beams at an angle to the rolling direction. The VAM features a special capability to be able to simultaneously detect the reflected beams in the longitudinal direction and in the transverse direction in one operation. It then calculates the refraction angles of the transmitted beam ($\theta 1$) and the reflected beam ($\theta hd\ c$) in the primary rolling direction.

The data input means 2 enters data such as the values of velocities $C_{sl}$ and $C_{sc}$ into computing means 4, which enters them in memory means 5.

Instruction means 3 includes keyboard and other means to enable the computer programs to operate.

Computing means 4 comprises facilities with computing capabilities and comprises evaluation means SP11, SP12 and SP13. The SP11 determines the acoustic anisotropy based on velocity ratio ($C_{sl}/C_{sc}$) or STB acoustic speed ratio ($C/V_{stb}$) in which one or both acoustic speed ratios of ($C_{sl}/C_{sc}$) and ($C/V_{stb}$) of the STB is calculated according to the output data from detection means; and the deviation in the refraction angle ($\theta - \theta_{stb}$) is calculated from the STB acoustic speed ratio ($C/V_{stb}$) or from the acoustic speed ratio $C_{sl}/C_{sc}$. The SP 12 and SP 13 evaluate the acoustic anisotropy based on the difference of the refraction angles ($\theta 1 - \theta_c$) where $\theta 1$ is the refraction angle in the rolling direction, and $\theta_c$ is the angle perpendicular to the rolling direction.

Memory means 5 comprises such data storage facilities as DRAM with instant read/write capabilities, and stores data such as the measurements by detection means 1, processed values from the computing means 4 as well as data bases such as specified testing conditions.

The data output means 6 outputs such data as measurement data obtained from the data input means 2, processed data from the computing means 4 and stored data from the memory means 5.

The display means 7 includes such facilities as LCD and digital devices to display data from data input means 2, processed data from the computing means 4 and stored data from the memory means 5.

Figure 2:
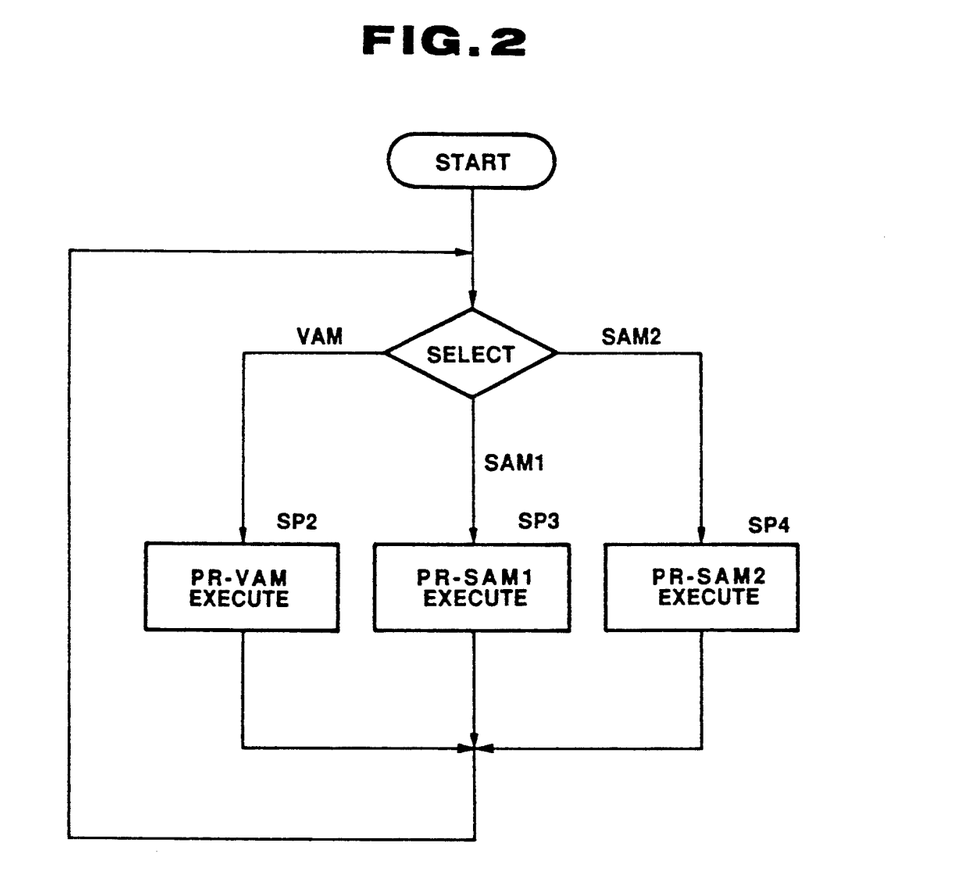
FIG. 2 is a generic flow chart for acoustic anisotropy determination.
Figure 3:
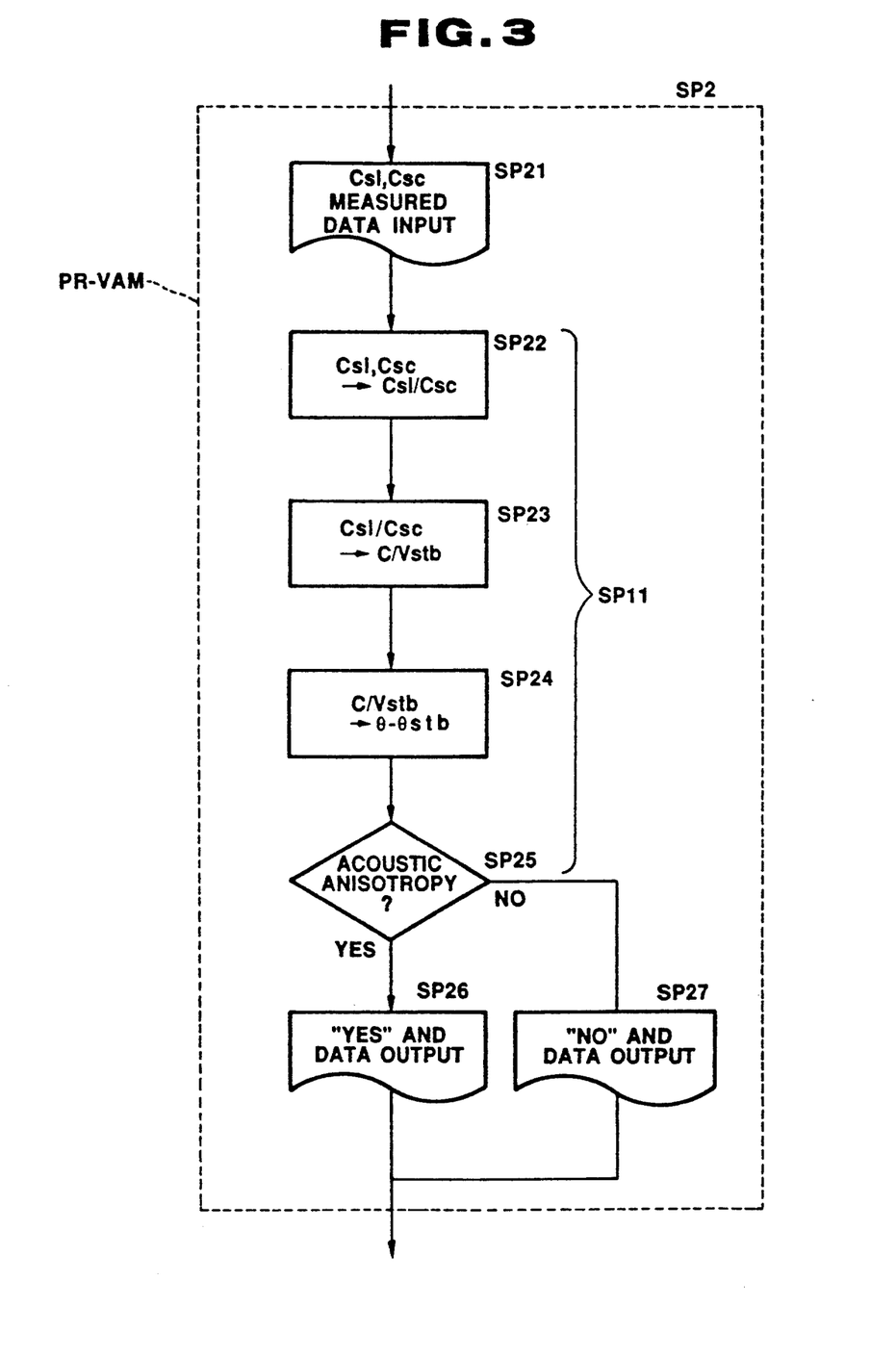
FIG. 3 is a flow chart for a computer program to determine acoustic anisotropy by the vertical shear wave probe method.
Figure 4:
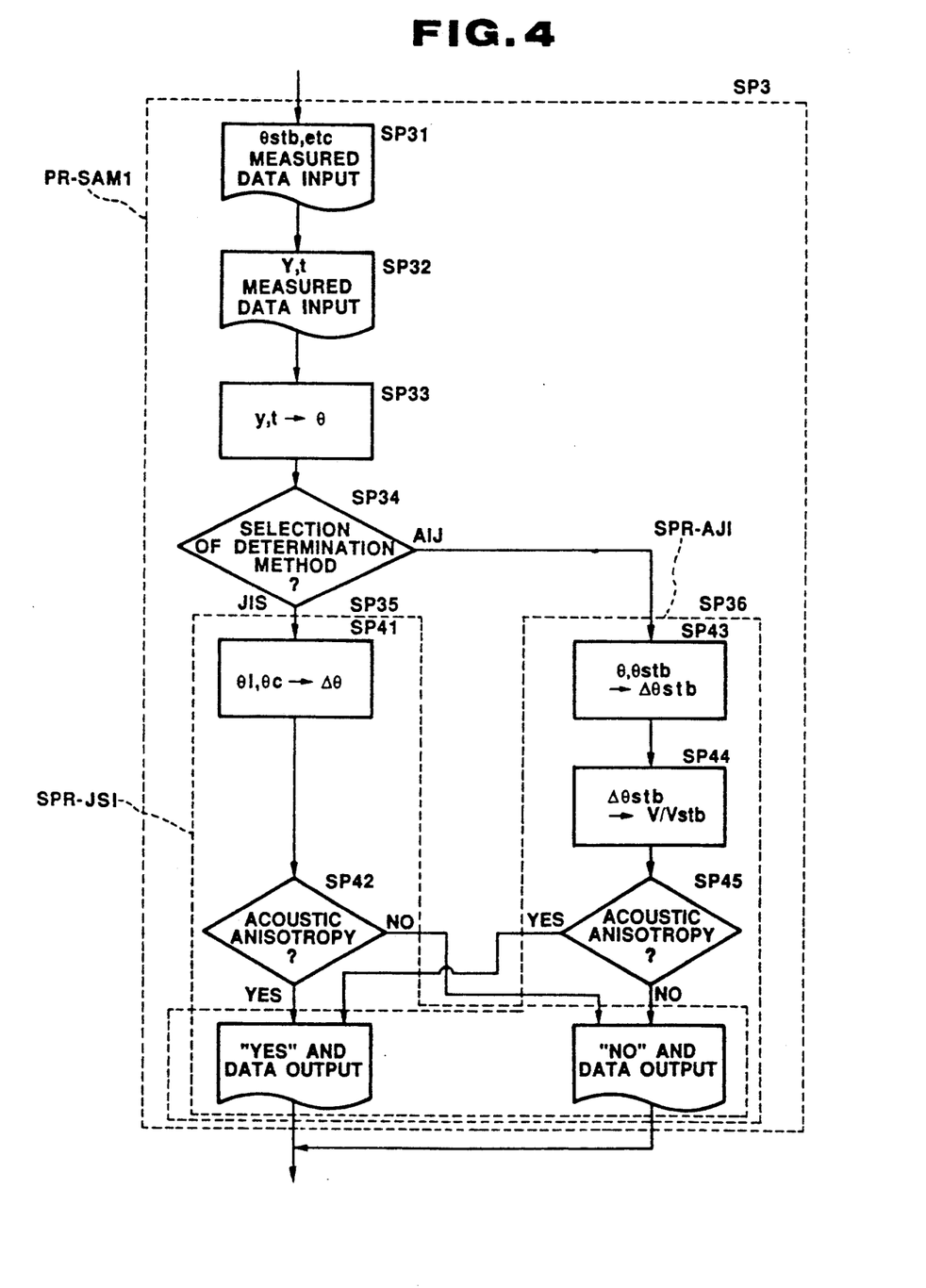
FIG. 4 is a flow chart for a computer program to determine acoustic anisotropy by the angle probe method.

Next, the operation of the invented acoustic anisotropy determining apparatus A is illustrated by means of flow charts shown in FIGS. 2 to 4.

First, the overall system of the apparatus is explained in the flow chart shown in FIG. 2.

By means of the instruction means 3, the first step SP1 selects one of the three measuring methods: a method based on the VAM probe; a method based on one angle probe (shortened to SAM 1); a method based on two angle probes (shortened to SAM 2).

Figure 6:
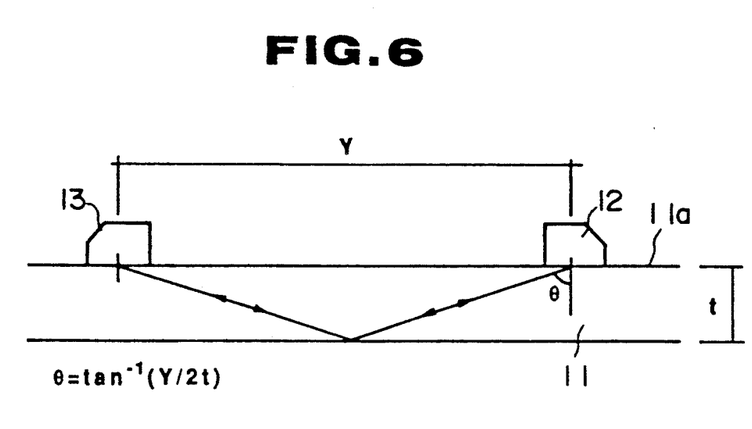
FIG. 6 is an illustration of a single probe method.

SAM 1 is an improved procedure of the JIS method of two angle probes in combination with V through scanning. This method consists of placing a transmitter angle probe 12 at a distance away from a receiver probe 13, and aligning the probe 12 in the direction of a flaw to be detected, on the top surface 11a of a steel component 11, as shown in FIG. 6. An ultrasonic beam of pulses is injected into the steel component 11 at an angle 0, and the position of the angle probe 12 is adjusted so as to obtain a maximum amplitude of echo reflected from the receiver probe 13. The angle $\theta$ is given by the following relationship between the thickness t of the steel component 11 and the distance Y, between the transmitter probe 12 and the receiver probe 13.

$$\theta \times \tan^{-1}(Y/2t)$$

At this stage, if "VAM" is selected by means of instruction means 3, step SP 2 is activated to operate the vertically acting shear wave program "PR-VAM"; if "SAM1" is selected, the active program is "PR-SAM1" at SP3; and if "SAM2" is selected, the active program is "PR-SAM2" at SP4.

Next, the method of determining the degree of acoustic anisotropy in construction materials by means of the apparatus A and the method of VAM will be explained in reference to the flow chart shown in FIGS. 2 and 3 and other relevant figures for each method.

(VAM-a) Preparation for measurements

Figure 7:
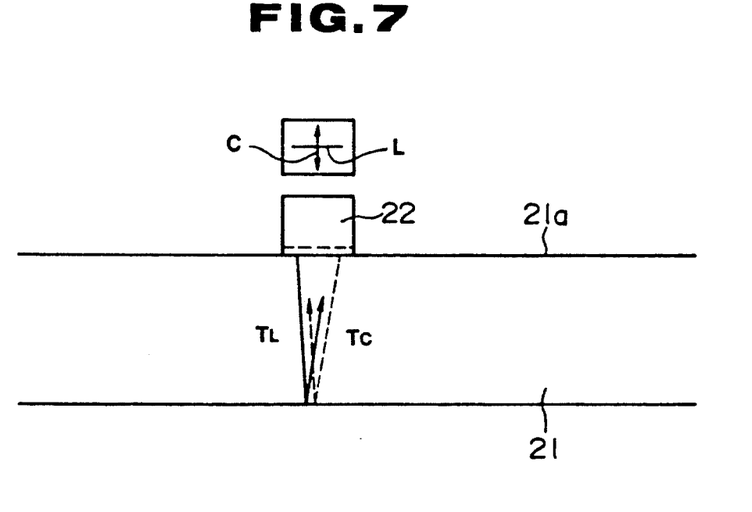
FIG. 7 is an illustration of a vertical probe method.

The arrangement of the probes for the VAM is shown in FIG. 7, in which a vertically acting probe 22 (first detection means) is placed on the upper edge 21a of the steel material 21. One of the acoustic vibration elements 22 is aligned with the main rolling direction of the material 21.

(VAM-b) Measurements, Data Input, Data Memory

By means of the instruction means 3, VAM is selected, which further selects a program "PR-VAM"in SP2. This program allows the probe 22 to inject into the material 21 mutually-perpendicular acoustic pulses one of which is aligned with the main rolling direction of the material 21, and to calculate the velocities of the reflected pulses from the two directions ($C_{sl}$ and $C_{sc}$).

Next in SP21, the measured data, such as $C_{sl}$, $C_{sc}$, and other data picked up by the probe 22, are entered into the computing means 4 through the input means 2, and the data are stored in the memory section 5 of computing means 4.

(VAM-c) Determination of $C_{sl}/C_{sc}$ In SP22, computing means 4 calculates the value of $C_{sl}/C_{sc}$ based on the results of measurements of $C_{sl}$ and $C_{sc}$.

(VAM-d) Determination of $C/V_{stb}$ in STB

Figure 8:
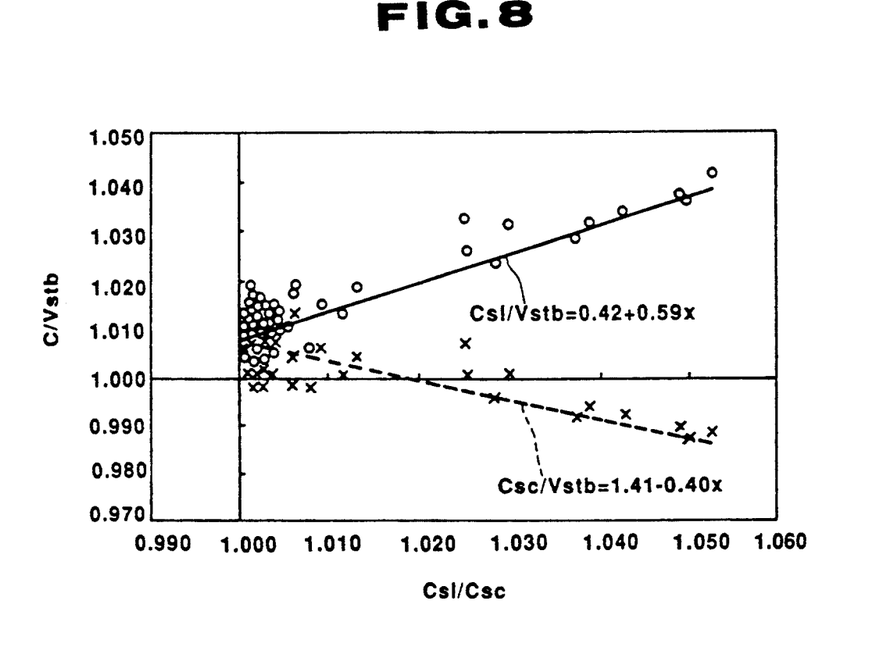
FIG. 8 is a graph showing the relationship between ($C_{sl}/C_{sc}$) and the velocity ratios in STB ($C/V_{stb}$).
Figure 9A:
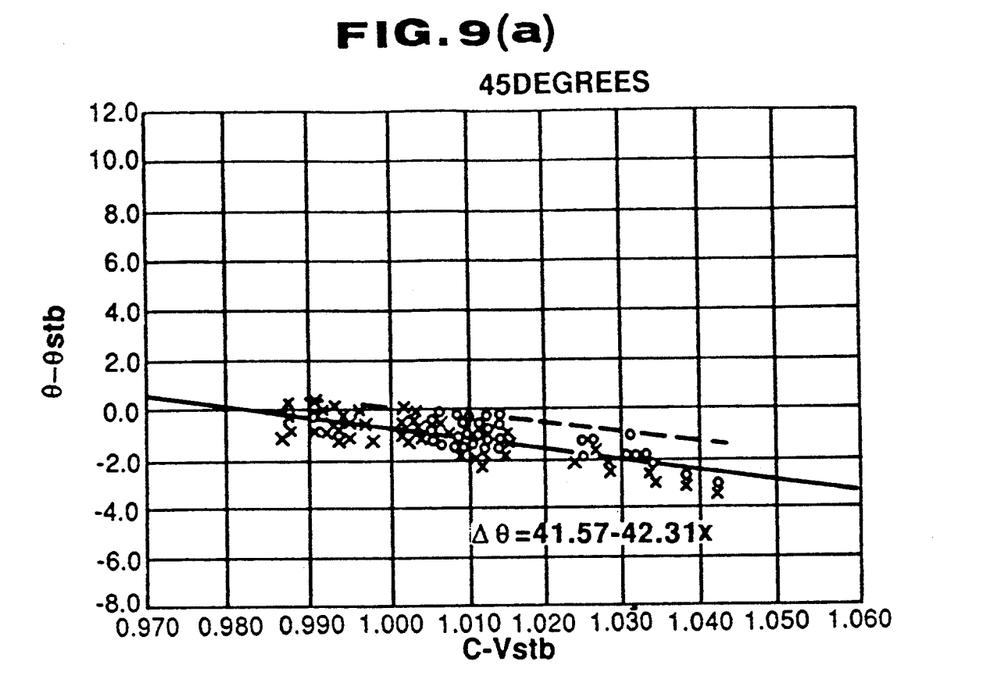
Figure 9B:
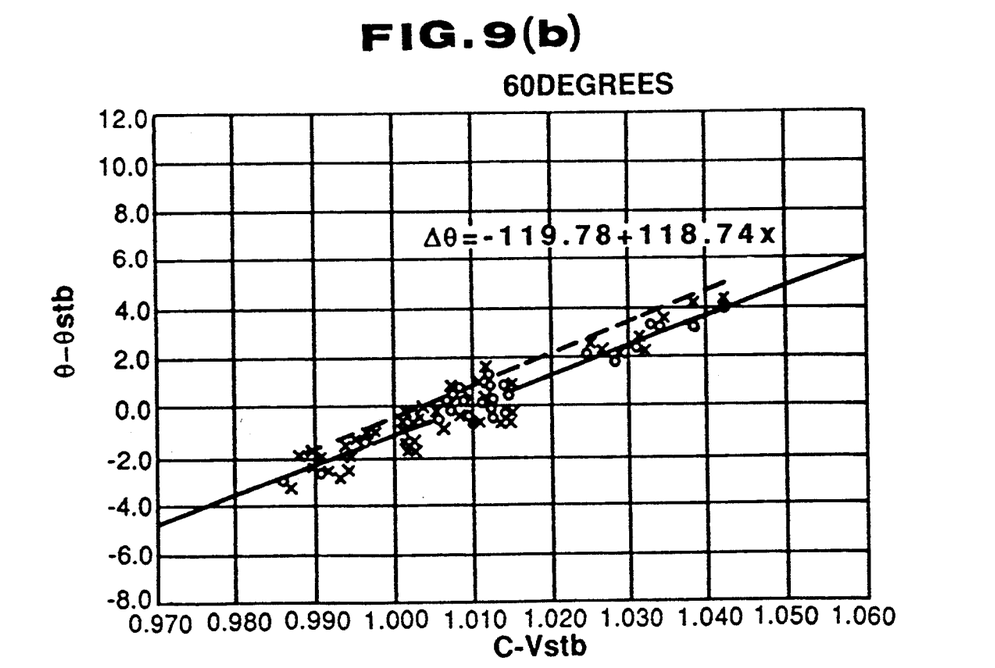
Figure 9C:
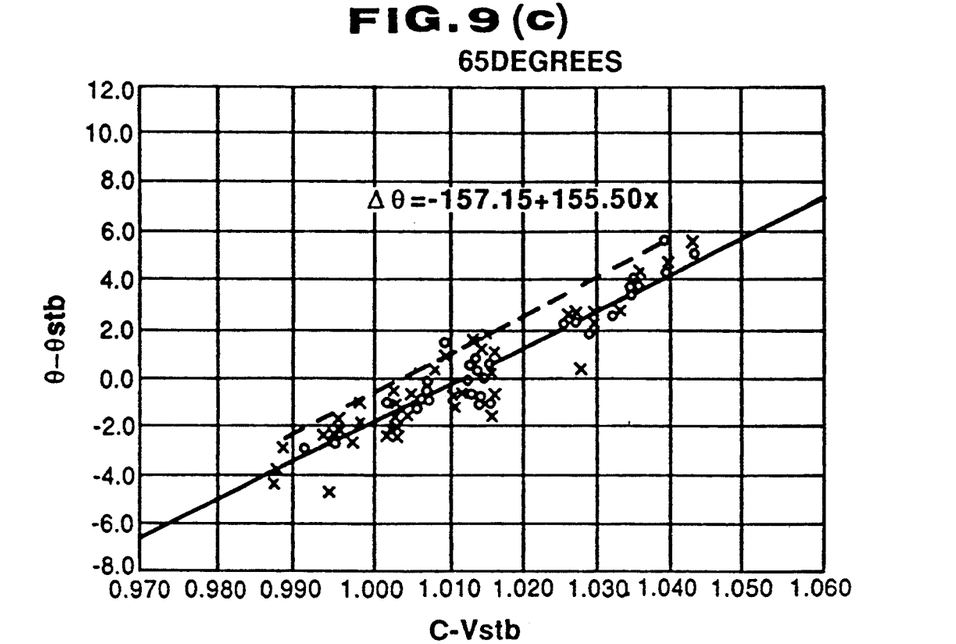
Figure 9D:
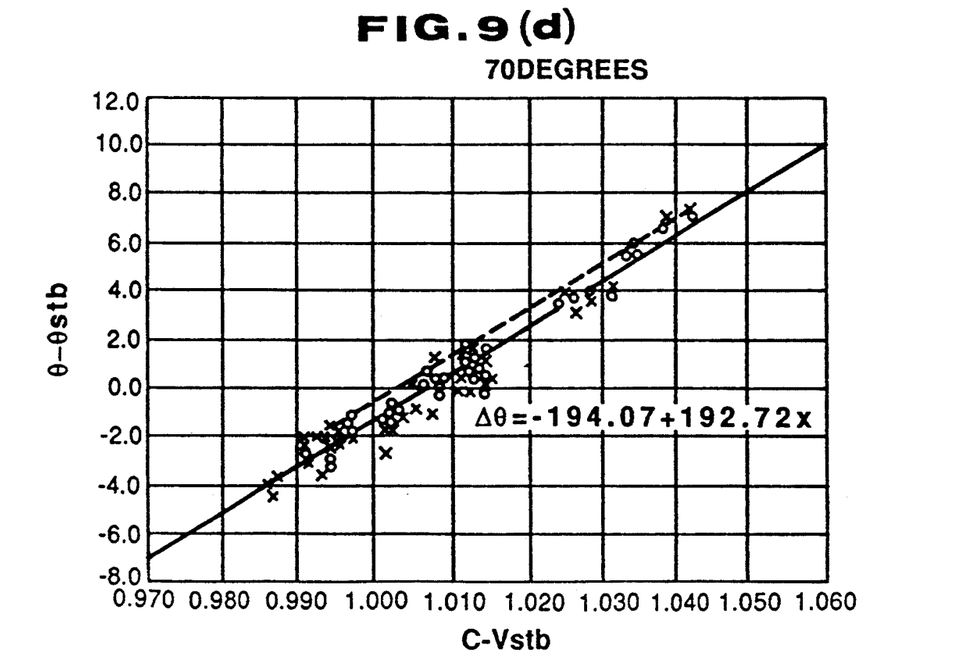

In SP23, by using the previously determined experimental relationship, shown in FIG. 8, between the speed ratios of acoustic beams in the material ($C_{sl}/C_{sc}$) and that in the STB ($C/V_{stb}$), the value of speed ratio in the STB ($C/V_{stb}$) is obtained from the measured speed ratio of the material ($C_{sl}/C_{sc}$), (VAM-e) Determination of the Deviations in Angle of Refraction ($\theta - \theta_{stb}$) of the STB In SP24, the deviations in the angle of refraction ($\theta - \theta_{stb}$) of the STB are obtained from the measured value of the STB speed ratio ($C/V_{stb}$) by the computing means 4 according to the experimental relationship shown in FIG. 9, between the STB speed ratio ($C/V_{stb}$) and the deviation in the angle of refraction ($\triangle = 74 - \theta_{stb}$).

(VAM-f) Determination of Acoustic Anisotropy

In SP25, the computing means 4 determines the degree of acoustic anisotropy according to JIS or to AIJ, based on the measurement of acoustic speed ratio ($C_{sl}/C_{sc}$) obtained in SP22 or of STB speed ratio ($C/V_{stb}$) obtained in SP23. When the computed ratio falls outside the value specified in the JIS, it is decided that there is acoustic anisotropy (YES), and when the ratio falls within the value, it is decided that there is no acoustic anisotropy (NO). The steps SP22 to 25 constitute SP11 in the evaluation step SP11.

(VAM-g) Data Memory, Input/Output and Display

The data from the foregoing evaluation step SP11 (corresponding to SP21 to 25 inclusively) are stored in the memory means 5, from which desired data are displayed on display means 7 through data input/output means 6.

By following the process described above, it is possible to evaluate, according to VAM, whether there is acoustic anisotropy in steel materials 21 with the use of the acoustic anisotropy determining apparatus "A".

Next, based on the above evaluation of the acoustic anisotropy in the material 21, search is made of defects in a welded joint in the material 21 using the conventional detection apparatus and angle probe 12. To determine the weld defect or the position of such a defect, the angle of refraction of STB from the angle probe 12 is corrected by the amount of deviation $(\theta - \theta_{stb})$ obtained from the above procedure.

Next, the procedure of determining the degree of acoustic anisotropy using the apparatus A according to the one angle probe (SAML) method is explained in reference to the flow charts shown in FIGS. 2 to 4.

(SAM1-a) Selection of Program PR-SAM1

In SP3, select "SAM1" by means of instruction means 3 and load the program "PR-SAM1".

(SAM1-b) Adjustments of Measurement Range and Measurement of STB Refraction Angle By means of the conventional acoustic apparatus and an angle probe 12 (detection means No. 2), adjustments of measurement range and the angle of refraction of STB ($\theta_{stb}$) are made, and in SP31 the data are entered into the computing means 4 through the input means 2. The input data are stored in memory means 5.

(SAM1-c) Preparation for Measurement

As shown in FIG. 6, on the upper surface 11a of the steel material 11, place the angle probe 12 and acrylic receiver probe 13 at some distance.

(SAM1-d) Determination of Beam Injection Distances And The Thickness t Of The Material Ultrasonic beam of pulses are injected into the steel component 11 at an angle to the direction of presumed defect, and the position of the angle probe 12 is adjusted so as to obtain a maximum amplitude of echo reflected from the receiver probe 13, thus yielding a value of the injection distance Y. In SP32, the above value Y and the thickness t of the steel material 11 are entered into the computing means 4 through data input means 2, and the data are stored in the memory means 5.

(SAM1-e) Determination of the Refraction Angle ($\theta$)

In SP33, the computing means 4 calculates the angle of refraction ($\theta$) from the following equation by substituting the injection distance (Y), the thickness of the steel material (t) into the equation $$\theta = \tan^{-1}(Y/2t)$$

(SAM1-f) Selection of Methodology for Determining the Degree of Acoustic Anisotropy In SP34, choose either the JIS or the AIJ method for determining the degree of acoustic anisotropy. The selection is made by means of instruction means 3, and if the JIS method is chosen, a subprogram SPR-JS1 becomes operative in SP35, and if AIJ is chosen, the other subprogram SPR-AJ1 becomes operative in SP36. Both of these methodologies will be explained, starting with the JIS method, executed in the subprogram SPR-JSL in SP35.

(SAM1-g) Determination of the Difference ($\theta$) in the Refraction Angle ($\theta$)

Figure 5A:
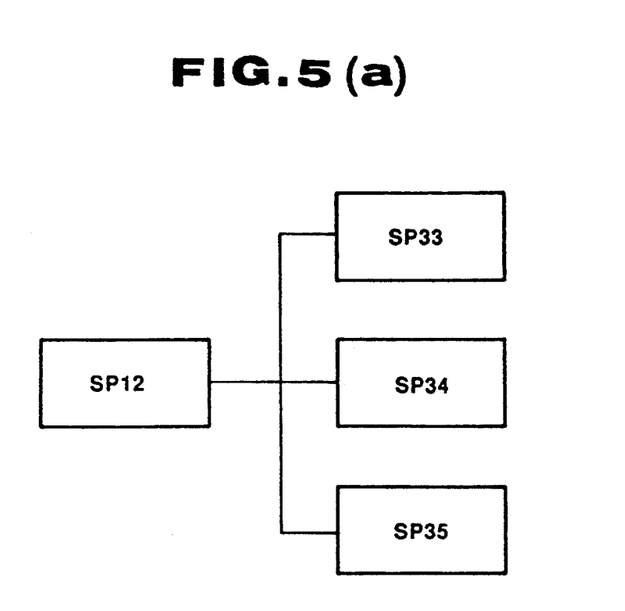

In SP41, obtain the difference ($\theta$) between the values of the refraction angle ($\theta$1) in the main rolling direction (direction L) and that ($\theta_C$) in the transverse direction (direction C) of the steel material 11.

(SAM1-h) Determination of the Degree of Acoustic Anisotropy

In SP42, the value of $\theta$ obtained by the computing means 4 in SP41 is compared with the JIS values to determine the degree of acoustic anisotropy in the material. When the measured value exceeds the specified value, it is decided that there is anisotropy (YES), and when the measured value is within the specified value, it is decided that there is no anisotropy (NO). The steps SP33 to 35 constitute the decision step SP12.

(SAM1-i) Data Memory, Input/output and Display

The data obtained in the decision step SP12 are placed in the memory means 5 by the computing means 4 and are displayed on display means 7 as needed through the input/output means 6.

Figure 5B:
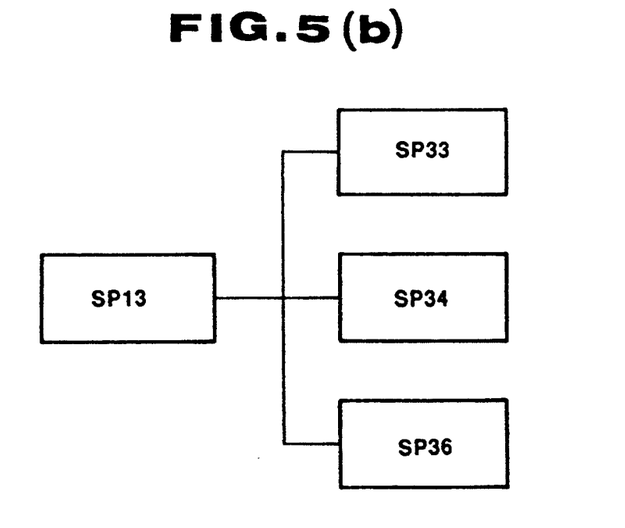

Next, the step SP36 for the AIJ method and subprogram SPR-AJ1, will be explained.

(SAM1-j) Determination of the Refraction Angle Difference of the STB ($\triangle \theta_{stb}$)

In SP43, the difference between the values of the measured refraction angle ($\theta$) and that of the STB ($\theta_{stb}$) is obtained by means of the computing means 4, and this value is designated as ($\triangle \theta_{stb}$) for the STB.

(SAM1-k) Determination of the Ratio (V//V$_{stb}$)

In SP44, the sound velocity ratio (V//V$_{stb}$) is obtained by inserting the difference value ($\triangle \theta_{stb}$) of STB refraction angles into one of the following formulae suitable to the angle probe 2 being used.

Case 1  $59° \geq \theta_s \leq 61°$ $V/V_{stb} = (119.14 + \theta_{stb})/117.46$ Case 2  $64° \geq \theta_s \leq 66°$ $V/V_{stb} = (170.70 + \theta_{stb})/169.44$ Case 3  $69° \geq \theta_s \leq 71°$ $V/V_{stb} = (184.67 + \theta_{stb})/183.03$ where $\theta_s$ is the mutual penetrating angle between the main pipe and a branch pipe.

(SAM1-l) Determining the Degree of Acoustic Anisotropy

In SP45, the determination of the degree of acoustic anisotropy is made, by means of the computing means 4, according to a comparison of the STB velocity ratio (V/V$_{stb}$) obtained in SP44 with those specified in the AIJ. When the STB ratio exceeds the specified value in the AIJ, it is determined that there is acoustic anisotropy (YES), and when it is within the specified value, there is no acoustic anisotropy (NO). The SP33, 34 and 36 constitute the evaluation step 13.

(SAM1-m) Data Memory, Input/output and Display

The data obtained in the determining step SP13 are placed in the memory means 5 by the computing means 4, and are displayed on display means 7 as needed through the input/output means 6.

By following the steps described above, it is possible to determine the degree of acoustic anisotropy in construction materials with the use of the anisotropy determining apparatus A and a single angle probe.

Next, test results are presented to confirm the operational effectiveness of the apparatus A.

Table 1 summarizes five modes of operation of the apparatus A evaluated during the above mentioned tests.

TABLE 1

| No. | Std. | Probe | Measure/Display Items |
|-----|------|-------|----------------------|
| K1  | AIJ  | VAM   | STB ratios (L,C)     |
| K2  | AIJ  | VAM   | STB ratios (L,C)     |
| K3  | AIJ  | SAM1  | Refraction Angles    |
| J1  | JIS  | VAM   | Velocity ratios      |
| J2  | JIS  | SAM1  | Refraction Angles    |

Table 2 shows the results of determining the degree of acoustic anisotropy according to the apparatus A and another popularly used apparatus X, and the extent of the agreement achieved between the two apparatuses.

TABLE 2

| No. | Anisotropy | No. of Trials A/X | Agreement % |
|---|---|---|---|
| K1 | YES | 13/12 | 97.5 |
|    | NO  | 27/28 |      |
| K2 | YES | 12/12 | 95.0 |
|    | NO  | 28/28 |      |
| K3 | YES | 8/7   | 97.2 |
|    | NO  | 28/29 |      |
| J1 | YES | 10/10 | 100.00 |
|    | NO  | 10/10 |      |
| J2 | YES | 9/10  | 95.0 |
|    | NO  | 11/10 |      |

These observations can be summarized as follows:

1. In the K1 mode, it was noted that the values of STB velocity ratio produced by the apparatus A tended to be lower by about 0.5% than those produced by the apparatus X, but the determination of the degree of acoustic anisotropy agrees well with each other at around 98%.

2. In the K2 mode, there is some difference in the results obtained by the two apparatuses. For this reason, the agreement is somewhat lower at 95%.

3. In the K3 mode, there is a tendency for the refraction angles measured by the apparatus A to be about 0.6° lower than that measured by the apparatus X. The agreement between the two apparatuses in the determination of the degree of acoustic anisotropy is 97%.

4. In the J1 mode, the velocity ratios between the two apparatuses agree extremely well. This leads to a perfect agreement between the two methodologies of determining the degree of acoustic anisotropy.

5. In the J2 mode, the refraction angles measured by the two apparatuses show a difference of about ±1°. This leads to an agreement of 95% in the determination of the degree of acoustic anisotropy between the two apparatuses.

The above results demonstrate that the apparatus A is able to duplicate the results produced by the conventional equipment sufficiently well to be considered a practical unit.

What is claimed is:

1. An apparatus for evaluating acoustic anisotropy in a material having a primary rolling direction, said apparatus comprising:
   (a) a first pulse generating and detecting means comprising a traverse beam probe having a double-structure vibrating element of transmitting ultrasonic pulses in two mutually perpendicular directions into said material, one said direction being parallel to said primary rolling direction and the other said direction being perpendicular to said primary rolling direction, and means for simultaneously detecting ultrasonic pulses reflected back from both of said directions;
   (b) a second-pulse generating and detecting means comprising an angle probe for transmitting ultrasonic pulses into said material in a direction at an angle to a thickness direction of said material and detecting reflected ultrasonic pulses;
   (c) a computing means comprising:
      a first acoustic anisotropy determining part for calculating speeds at which ultrasonic pulses propagate in each of said mutually perpendicular directions within said material and comparing said speeds to determine the presence of acoustic anisotropy in said material,
      a second acoustic anisotropy determining part for calculating refracting angles for ultrasonic pulses transmitted by said second pulse generating and detecting means in each of said mutually perpendicular directions and comparing said angles to determine the presence of acoustic anisotropy in said material, and
      means for calculating a deviation between a retracting angle, calculated as aforesaid, and an a experimentally determined retracting angle stored as a function of acoustic speed;
   (d) means for selecting one of said acoustic anisotropy determining parts for use in determining the presence of acoustic anisotropy in said material; and
   (e) a display means for displaying results of an acoustic anisotropy determination, propagation speed ratios, refracting angles, and aforesaid deviation.

2. The apparatus for evaluating acoustic anisotropy in a test material according to claim 1, wherein said first pulse generating and detecting means and said second pulse generating and detecting means are housed in a common unit.

3. The apparatus for evaluating acoustic anisotropy in a material according to claim 1, wherein said first acoustic anisotropy determining part of said computing means comprises means for calculating a speed ratio of said ultrasonic pulses from speeds of ultrasonic pulses produced in said material in said two mutually perpendicular directions, and means for determining the presence of acoustic anisotropy in said material based on a speed ratio, so computed.

4. The apparatus for evaluating acoustic anisotropy in a material according to claim 1, wherein said second acoustic anisotropy determining part of said computing means comprises means for calculating a deviation between two refracting angles and means for determining the presence of acoustic anisotropy in said material based on said deviation.

5. The apparatus for evaluating acoustic anisotropy in a material according to claim 1, wherein said second acoustic anisotropy determining part is programmed for
   firstly calculating a deviation between a refracting angle of said material and predetermined experimental extracting angle data from a standard test block,
   secondly calculating a ratio of a speed of ultrasonic pulses propagating in said material to an experimentally determined speed of ultrasonic pulses propagating in a standard test block based on said deviation between the refracting angle of said best material and predetermined experimental retracting angle data from a standard test block, and
   then determining whether acoustic anisotropy is present in said material based on the velocity ratio.

6. The apparatus for evaluating acoustic anisotropy in a material according to claim 3, wherein said computing means comprises means for indicating the presence of acoustic anisotropy when said speed ratio is higher than 1.02.

7. The apparatus for evaluating acoustic anisotropy in a material according to claim 4, wherein said means for determining comprises means for indicating the presence of acoustic anisotropy when said deviation of refracting angles is greater than 2.

* * * * *

UNITED STATES PATENT AND TRADEMARK OFFICE
CERTIFICATE OF CORRECTION

PATENT NO. : 5,305,641
DATED : April 26, 1994
INVENTOR(S) : Mitsugu Kuramochi, Yoshitaka Yabe It is certified that error appears in the above-indentified patent and that said Letters Patent is hereby corrected as shown below:

Column 9, Claim 1, line 51, "of" should be --for--.

Column 10, Claim 1, line 11, delete "a".

Column 10, Claim 5, line 47, "extracting" should be --refracting--;

line 54-55, "retracting" should be --refracting--.

Signed and Sealed this

Sixth Day of September, 1994

Attest:

BRUCE LEHMAN

*Attesting Officer*     *Commissioner of Patents and Trademarks*